United States Patent
Randall et al.

(10) Patent No.: US 8,241,350 B2
(45) Date of Patent: *Aug. 14, 2012

(54) ANCHORING DEVICE FOR AN ENDOLUMINAL PROSTHESIS

(75) Inventors: Scott L. Randall, Mesa, AZ (US); William R. Bratt, Tempe, AZ (US)

(73) Assignee: Bard Peripheral Vascular, Inc., Tempe, AZ (US)

( * ) Notice: Subject to any disclaimer, the term of this patent is extended or adjusted under 35 U.S.C. 154(b) by 39 days.

This patent is subject to a terminal disclaimer.

(21) Appl. No.: 13/009,727

(22) Filed: Jan. 19, 2011

(65) Prior Publication Data

US 2011/0118823 A1 May 19, 2011

Related U.S. Application Data

(63) Continuation of application No. 11/966,203, filed on Dec. 28, 2007, now Pat. No. 7,887,580, which is a continuation of application No. 10/079,155, filed on Feb. 20, 2002, now Pat. No. 7,331,992.

(51) Int. Cl.
*A61F 2/06* (2006.01)

(52) U.S. Cl. ...................................... 623/1.36; 623/1.15
(58) Field of Classification Search ................. 623/1.13, 623/1.14, 1.15, 1.36, 1.37
See application file for complete search history.

(56) References Cited

U.S. PATENT DOCUMENTS

| | | | | |
|---|---|---|---|---|
| 6,287,335 B1 * | 9/2001 | Drasler et al. | ............... | 623/1.28 |
| 7,331,992 B2 * | 2/2008 | Randall et al. | ............... | 623/1.36 |
| 7,887,580 B2 * | 2/2011 | Randall et al. | ............... | 623/1.36 |
| 2001/0001317 A1 * | 5/2001 | Duerig et al. | ................ | 623/1.15 |

* cited by examiner

*Primary Examiner* — Tuan V Nguyen
*Assistant Examiner* — David Eastwood
(74) *Attorney, Agent, or Firm* — Rutan & Tucker, LLP

(57) ABSTRACT

An endoluminal prosthesis including a radially expandable frame and an anchoring member. The anchoring member includes a first arm attached to a first strut of the frame and a second arm attached to a second adjacent strut of the frame. The first arm is joined to the second arm to form a vessel engaging end that, together with at least a portion of the first arm and second arm, is directed toward a central axis of the frame in the frame's collapsed configuration.

18 Claims, 3 Drawing Sheets

ANCHORING DEVICE FOR AN ENDOLUMINAL PROSTHESIS

PRIORITY

This application is a continuation of U.S. patent application Ser. No. 11/966,203, filed Dec. 28, 2007, now U.S. Pat. No. 7,887,580, which is a continuation of U.S. patent application Ser. No. 10/079,155, filed Feb. 20, 2002, now U.S. Pat. No. 7,331,992, each of which is incorporated by reference into this application as if fully set forth herein.

FIELD OF THE INVENTION

This invention relates generally to a device for preventing the migration of an endoluminal prosthesis and more particularly to a device that is incorporated into and protrudes outward from an endoluminal prosthesis upon deployment thereof within a body lumen.

BACKGROUND OF THE INVENTION

Endoluminal prostheses such as stents, stent-grafts and other related devices are used to treat vessels that have become weakened or diseased. These prostheses are used in a variety of circumstances to provide a remedy for the damaged vessels. The remedy can come in the form, for example, of added support for a vessel that has become weakened as a result of an aneurysm. In particular, in the case of an abdominal aortic aneurysm (AAA), in which a portion of a patient's aorta, the major artery carrying blood from the heart, has developed a weakened wall, a graft is inserted to span the weakened region to facilitate a blood flow path between the healthy portions of the aorta.

In order to reduce the risk involved with invasive abdominal surgery, in which the patient's abdominal cavity is opened so that the graft can be sutured in place, many methods of percutaneous placement have been developed. Accompanying percutaneous placement, however, is a need to maintain the graft in its inserted position in the absence of sutures. To this end, various anchoring devices have been proposed, most of which are attached to, or incorporated in, the graft. Examples of prior art anchoring devices include those found in U.S. Pat. No. 5,843,167, in the form of an assembly that is attached to the graft. The assembly includes anchors which are attached to a graft on either end and which are connected by wire struts that extend along the length of the graft. These anchors have hooks that are formed on the end of short segments of wire that are secured to the anchor. The hooks are adapted to protrude radially outwardly upon deployment of the endoprosthesis, extending a short distance beyond the bends of the anchor.

U.S. Pat. No. 5,843,164 also discloses an anchoring system that includes hooks to penetrate the aortic wall. The hooks are generally provided at each end of the stent graft, each hook having one or more barb thereon. U.S. Pat. No. 5,591,197 discloses a different type of anchor in the form of deformable connecting members that attach cylindrical elements which together form a stent. Upon balloon expansion of the connecting members, a notched, weakened area is forced outward to form a barb to penetrate the aortic wall. Finally, U.S. Pat. No. 5,593,434 discloses a plurality of projections or teeth cut away from a sheet of material, which is curled into a cylinder to form a stent.

The drawback to these and other anchoring systems is that the teeth or hooks attached or integrated into the grafts or stents have a tendency to catch on the delivery sheaths or catheters during deployment. This creates problematic situations in the deployment process as the teeth or hooks tear the sheath material, preventing the necessary precision required in percutaneous delivery into a body lumen.

Thus, it would be desirable to provide an anchoring device for an endoluminal prosthesis, which will forcefully engage the vessel wall upon deployment and be configured so that contact with the delivery sheath or catheter upon insertion of the prosthesis is avoided.

BRIEF SUMMARY OF THE INVENTION

The invention enables the anchoring of an endoluminal prosthesis to prevent migration thereof in a reliable way without the problems associated with intraluminal delivery of the prosthesis. In particular, the invention allows smooth, efficient delivery of the prosthesis by providing an anchoring system that does not engage the delivery catheter or sheath upon deployment of the prosthesis within a body lumen.

In one embodiment, an anchoring device for an endoluminal prosthesis includes a tubular-shaped body having a plurality of struts, each strut having a proximal end and a distal end, wherein adjacent struts are connected by a connecting portion at one of said proximal end and distal end such that said body comprises a plurality of proximal connecting portions and a plurality of distal connecting portions, and an anchoring member positioned proximate at least one of said connecting portions, the anchoring member comprising an apex formed by the joining of a first arm and a second arm, wherein the first arm is attached to a first of said adjacent struts and the second arm is attached to a second of said adjacent struts.

DETAILED DESCRIPTION OF THE INVENTION

The following detailed description illustrates the invention by way of example, not by way of limitation, the principles of the invention. This description will clearly enable one skilled in the art to make and use the invention, and describes several embodiments, adaptations, variations, alternatives and uses of the invention, including what we presently believe is the best mode of carrying out the invention.

The invention will be described by way of illustration with reference to a particular application of the present invention, namely for use with a AAA prosthesis. One of skill in the art should appreciate, however, that the present invention could equally be utilized in countless other endoluminal prostheses, such as bare stents.

Figure 1:
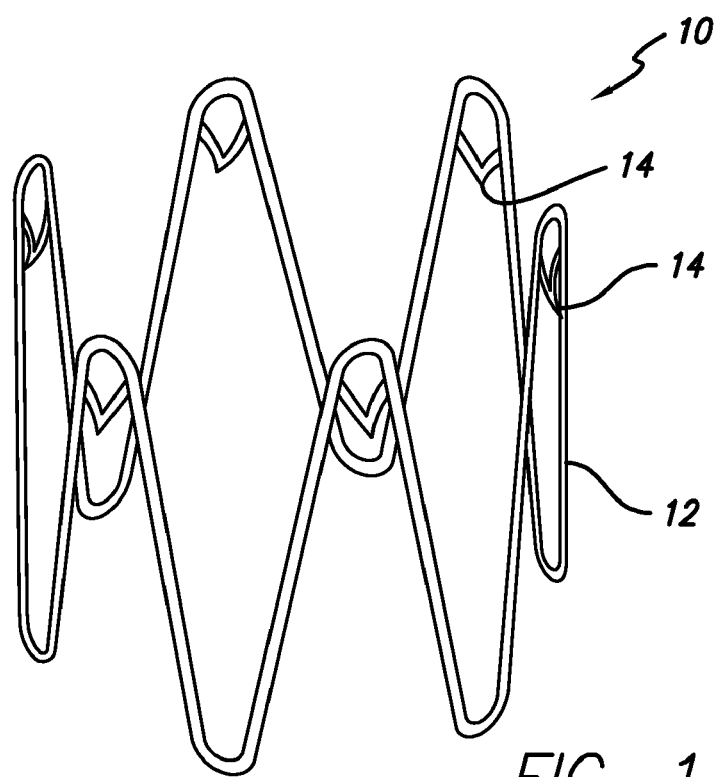
FIG. 1 illustrates a perspective view of an end portion of a stent with the inventive anchoring system attached thereto in a deployed state.
Figure 2:
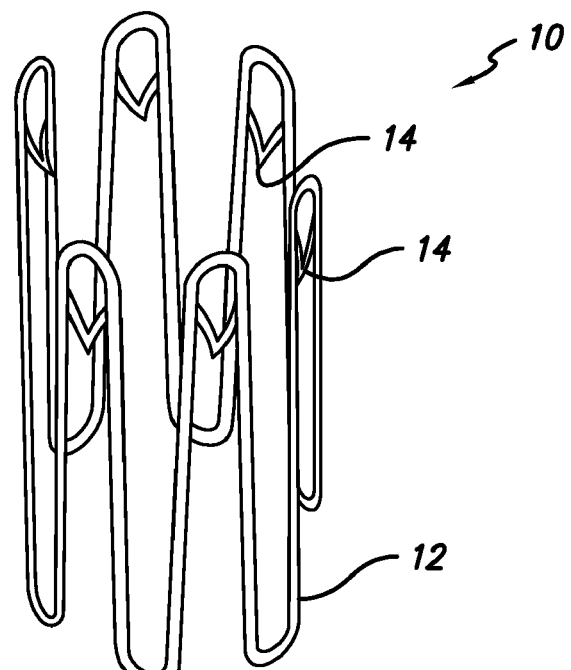
FIG. 2 illustrates FIG. 1 in a contracted state for intraluminal delivery.

Referring now to FIG. 1, a preferred embodiment of the anchoring system of the present invention is illustrated. A ring stent 10 is shown having a body portion 12 and anchors 14. As shown in FIG. 1, the ring stent 10 is illustrated in its deployed or enlarged diameter state. In this enlarged state, the anchors 14 point away from the inner portion of the ring stent 10 for attachment within a blood vessel. FIG. 2 shows the ring stent 10 in a collapsed or contracted state for implantation within a delivery catheter or sheath (not shown). It should be noted that the anchors 14 in this contracted state point inward toward a central axis of the stent 10 to avoid tearing or damaging the catheter or sheath as it is withdrawn.

In addition to the benefits provided by the anchoring system of the present invention with regard to maintaining the integrity of the delivery catheter or sheath and thereby preventing associated problems thus presented, such as difficulty with placement of the device, the anchoring system is also optimal for preventing migration of the endoluminal prosthesis with which it is associated.

Referring again to FIGS. 1 and 2, the delivery process will be described in more detail. The stent 10 is initially in a dormant position when in its contracted state during percutaneous insertion into a patient's vessel, as shown in FIG. 2. The stent 10 can be maintained in this dormant state in a number of ways, including, for example, physical constraint imposed by a delivery catheter or sheath and temperature induced restraint (when the stent is made of shape memory material). Upon reaching the predetermined site within the vessel for deployment of the stent 10 or prosthesis to which the stent 10 is incorporated, a delivery catheter will be withdrawn, generally by sliding off of the stent 10. Because of this sliding action of the catheter or sheath, which is usually made of a soft material, it is important that no sharp edges engage the sheath. As stated above, the stent 10 is advantageously designed with the sharp portion of the anchors 14 pointing inward toward a central axis of the stent 10 to address this concern. When the catheter or sheath is withdrawn and the constraint is removed, the stent 10 expands to an expanded diameter shown in FIG. 1. As the stent 10 expands, the anchors 14 "spring" outward to secure the stent 10 in place within the vessel.

The spring action of anchors 14 takes place due to its design, placement and make-up. In the preferred embodiment, the anchors 14 comprise a V-shaped member that is affixed to a stent. The V-shaped member can be attached to the stent separately or can be formed into the stent (see FIG. 5). Preferably, a plurality of V-shaped members are arranged around the circumference the stent as showed in FIGS. 1 and 2. The V-shaped members can be incorporated into ring stents as shown in FIGS. 1 and 2, or other types of stents, in which the V-shaped members can be placed around one or both of the ends and/or in the middle region thereof. The V-shaped members are preferably made of stainless steel, although in a shape memory stent the V-shaped members would preferably made from Nitinol. Of course, many other materials are available which would similarly provide a "springing" action outward upon expansion or deployment of the stent within the vessel.

Figure 3:
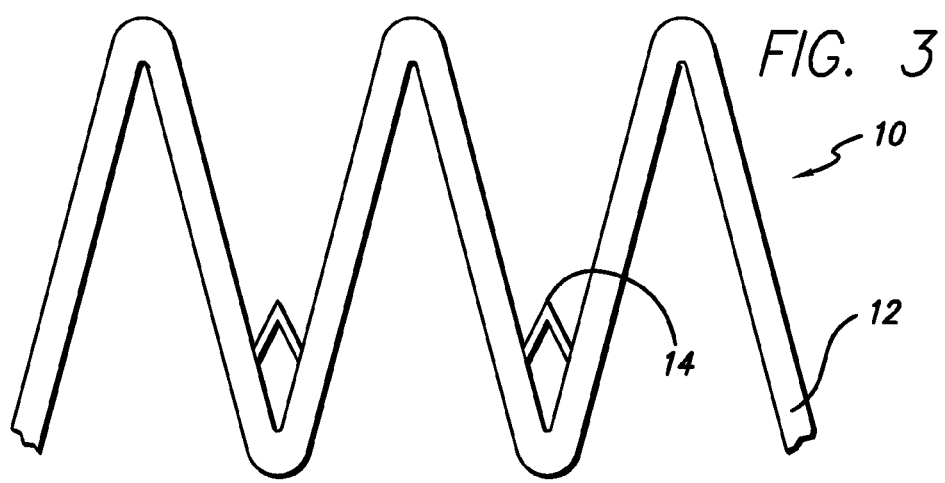
FIG. 3 is an enlarged view of the stent anchoring system in FIG. 1.

The springing action, as discussed, can be attributed to the material and shape of the anchor as well as the placement thereof within the stent. As depicted in FIG. 2, the anchors 14 are pointed toward a central axis of the stent 10. This occurs because the anchors 14 are positioned within the stent 10 when the stent 10 is in a relaxed state, as shown in FIG. 3. Due to the configuration of the anchors 14 in combination with the stiffness of the material, the anchors 14 will point in a respective direction (either outwardly or inwardly) when a force is applied to the stent 10, because the bending force will be transmitted along the length of the anchors 14 without bending at the tip of the anchor itself. This occurrence can be manipulated by altering the design and material selection of the anchor 14 to achieve a greater or lesser spring action.

Figure 4:
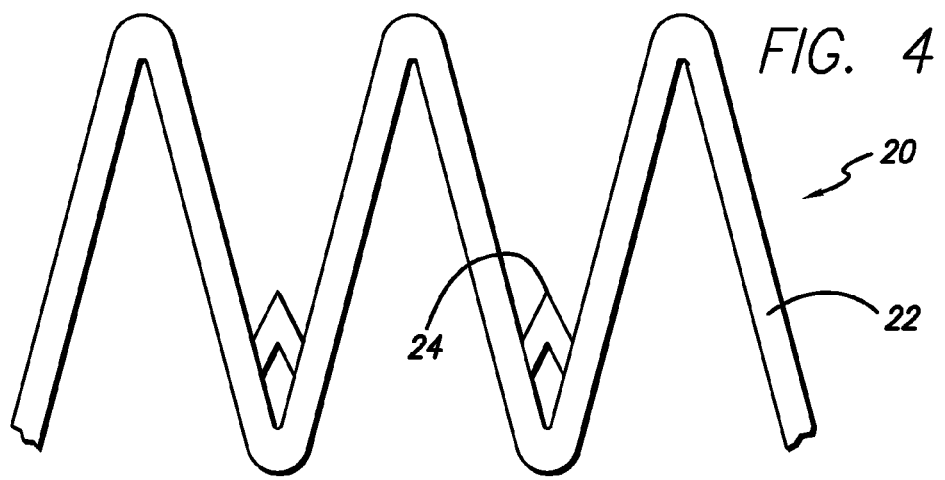
FIG. 4 is an enlarged view of an alternate embodiment of the anchoring system of the present invention.
Figure 5:
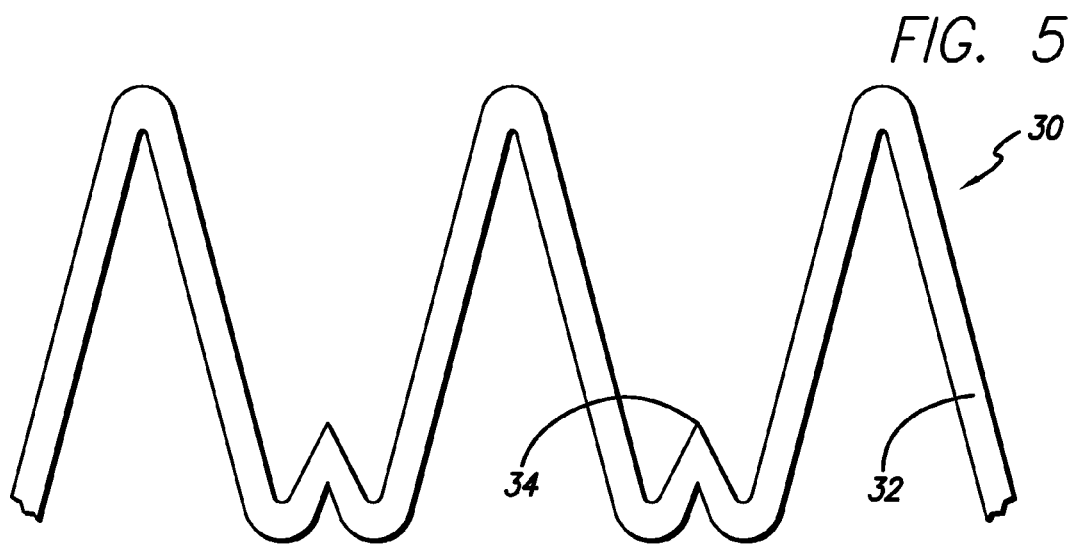
FIG. 5 is an enlarged view of another alternate embodiment of the anchoring system of the present invention.

FIGS. 4 and 5 show examples of alternate embodiments of the V-shaped members of the present invention. FIG. 4 illustrates a stent 20 with anchors 24, incorporated into stent body 22, the anchors 24 having a thicker body than that of anchor 14. FIG. 5 illustrates a stent 30 having anchors 34 that are integral with a stent body 32.

Figure 6:
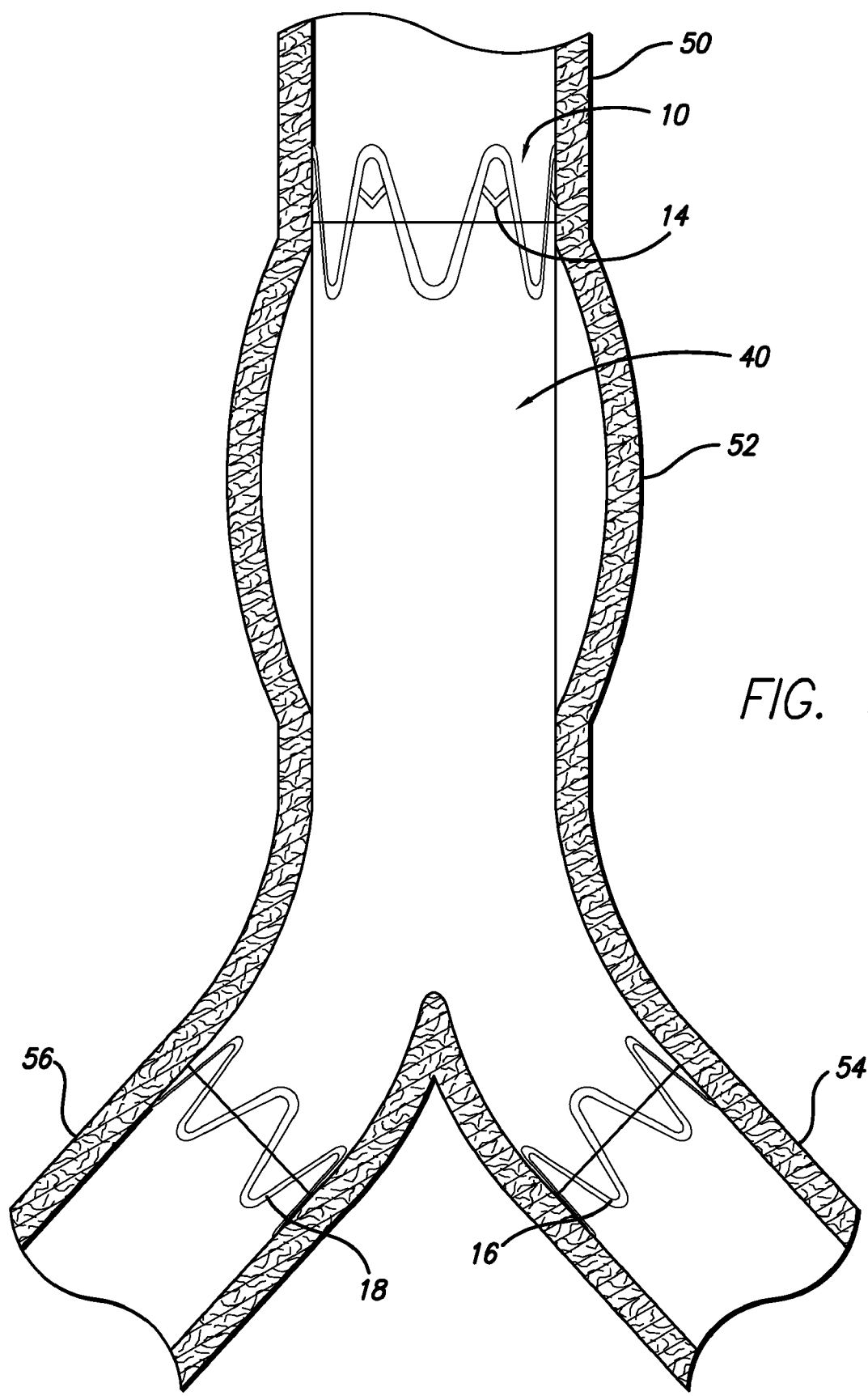
FIG. 6 is a view of a AAA device incorporating the anchoring system of the present invention as implanted.

FIG. 6 shows a portion of the abdominal aortic artery of a patient connected in its upper part with thoracic artery 50 and branching into two iliac arteries 54 and 56. The abdominal aorta presents an aneurysm 52. The stent 10 is incorporated into a AAA prosthesis 40 for treatment of the artery and is shown in its deployed condition so that anchors 14 are engaging the wall of the artery 50. In this embodiment, stents 16 and 18 hold the left and right legs of the prosthesis 40 in place within the iliac arteries 54 and 56. As shown, stents 16 and 18 do not have anchors incorporated therein although it is certainly possible in an alternate embodiment for all stents of the prosthesis 40 to have anchors. The anchors 14 incorporated in stent 10 hold the AAA prosthesis 40 in position within the artery and prevent migration thereof.

The present invention has been described above in terms of a presently preferred embodiment so that an understanding of the present invention can be conveyed. There are, however, many configurations for an anchoring system for endoluminal prostheses not specifically described herein but with which the present invention is applicable. The present invention should therefore not be seen as limited to the particular embodiments described herein, but rather, it should be understood that the present invention has wide applicability with respect to endoluminal prostheses generally. All modifications, variations, or equivalent arrangements and implementations that are within the scope of the attached claims should therefore be considered within the scope of the invention.

What is claimed is:

1. An endoluminal prosthesis, comprising
a radially expandable frame with a plurality of struts, including a first strut connected to a second strut, the frame having a fully collapsed configuration with a fully collapsed perimeter and a fully expanded configuration with a fully expanded perimeter larger than the fully collapsed perimeter; and
an anchoring member, including a first arm connected to the first strut and a second arm connected to the second strut, the first arm connected to the second arm to form a vessel engaging end that, together with at least a portion of the first arm and second arm, is directed toward a central axis of the frame in the fully collapsed configuration, forming an angle with respect thereto.

2. The endoluminal prosthesis according to claim 1, wherein the vessel engaging end and at least a portion of the first arm and second arm are directed away from the central axis of the frame in the fully expanded configuration, forming a deployed angle with respect thereto.

3. The endoluminal prosthesis according to claim 1, wherein the radially expandable frame is maintained in the fully collapsed configuration by a physical constraint external to the endoluminal prosthesis and imposed on the radially expandable frame.

4. The endoluminal prosthesis according to claim 3, wherein the vessel engaging end is directed toward the central axis of the frame in a natural state without being imposed upon by the physical constraint.

5. The endoluminal prosthesis according to claim 1, wherein the vessel engaging end is within the fully collapsed perimeter when the radially expandable frame is in the fully collapsed configuration.

6. The endoluminal prosthesis according to claim 1, wherein the vessel engaging end is outside the fully expanded perimeter when the radially expandable frame is in a fully expanded configuration.

7. The endoluminal prosthesis according to claim 1, wherein the struts are arranged in a zig-zag configuration and adjacent struts are connected by a connecting member.

8. The endoluminal prosthesis according to claim 7, wherein the connecting member is curved.

9. The endoluminal prosthesis according to claim 7, wherein the first arm and second arm are connected to respective struts proximate the connecting member between the respective struts.

10. The endoluminal prosthesis according to claim 1, wherein the anchoring member connects the first strut to the second strut.

11. The endoluminal prosthesis according to claim 10, wherein the first strut is directly connected to the first arm and the second strut is directly connected to the second arm, wherein connections between the first strut and the first arm and between the second strut and the second arm are in a direction generally opposite from the vessel engaging end, and wherein the first arm, first strut, second arm, and second strut together form a "W" shape.

12. An endoluminal prosthesis, comprising
a radially expandable frame with a plurality of struts, the frame having a collapsed configuration with a collapsed perimeter and an expanded configuration with an expanded perimeter larger than the collapsed perimeter; and
an anchoring member, including a first arm connected to a first strut and a second arm connected to a second strut, the first arm connected to the second arm to form a vessel engaging end that, together with at least a portion of the first arm and second arm, is directed toward a central axis of the frame in the collapsed configuration, forming an angle with respect thereto.

13. The endoluminal prosthesis according to claim 12, wherein the vessel engaging end and at least a portion of the first arm and second arm are directed away from the central axis of the frame in the expanded configuration, forming a deployed angle with respect thereto.

14. The endoluminal prosthesis according to claim 12, wherein the anchoring member extends from an end of the first arm and second arm such that the anchoring member is integral with the radially expandable frame.

15. The endoluminal prosthesis according to claim 14, wherein the vessel engaging end of the anchoring member is directed away from the end of the first arm and second arm such that the first arm and second arm are circumferentially co-extensive with a portion of the first strut and second strut.

16. The endoluminal prosthesis according to claim 12, wherein the vessel engaging end forms a "V" shape between the first arm and the second arm.

17. The endoluminal prosthesis according to claim 12, wherein the anchoring member forms a "W" shape with the first strut and second strut.

18. The endoluminal prosthesis according to claim 17, wherein connections between the first strut and the first arm and between the second arm and the second strut are curved.

* * * * *